(12) United States Patent
Sano et al.

(10) Patent No.: US 7,250,030 B2
(45) Date of Patent: Jul. 31, 2007

(54) CUFF FOR BLOOD PRESSURE MONITOR AND BLOOD PRESSURE MONITOR HAVING THE SAME

(75) Inventors: Yoshihiko Sano, Kyoto (JP); Hiroshi Kishimoto, Kyoto (JP); Hiromichi Karo, Kyoto (JP); Yoshinori Tsurumi, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 11/297,339

(22) Filed: Dec. 9, 2005

(65) Prior Publication Data

US 2006/0129049 A1 Jun. 15, 2006

(30) Foreign Application Priority Data

Dec. 10, 2004 (JP) ............................. 2004-358773

(51) Int. Cl.
*A61B 5/02* (2006.01)
(52) U.S. Cl. ........................................ 600/499; 600/490
(58) Field of Classification Search ........ 600/490–504, 600/481, 485
See application file for complete search history.

(56) References Cited

U.S. PATENT DOCUMENTS

| | | | |
|---|---|---|---|
| 4,667,672 A * | 5/1987 | Romanowski | 606/202 |
| 6,346,083 B1 * | 2/2002 | Nishibayashi et al. | 600/490 |
| 6,527,727 B2 * | 3/2003 | Itonaga et al. | 600/499 |
| 6,969,356 B2 * | 11/2005 | Nishibayashi | 600/499 |
| 2004/0186385 A1 | 9/2004 | Mochizuki | |

FOREIGN PATENT DOCUMENTS

| | | |
|---|---|---|
| EP | 1125551 A2 | 8/2001 |
| JP | 02-107226 A | 4/1990 |
| JP | 2001-224558 A | 8/2001 |
| JP | 2003-24286 A | 1/2003 |
| TW | 564168 | 12/2003 |

OTHER PUBLICATIONS

Taiwanese Office Action dated Novenber 16, 2006, directed to counterpart TW Application No. 094143304.

* cited by examiner

*Primary Examiner*—Charles A. Marmor, II
*Assistant Examiner*—Navin Natnithithadha
(74) *Attorney, Agent, or Firm*—Morrison & Foerster LLP

(57) ABSTRACT

A cuff for a blood pressure monitor is provided with an air bag including a first bag member located outside and a second bag member located inside in the thickness direction when fitted on a living body. The first and second bag members have first and second inflated/deflated spaces, respectively. The second bag member is formed by laying a single-layer resin sheet on the surface on the living body side of the first bag member and by melting and bonding its rim to the surface. A bonded portion of the first bag member with the resin sheet is positioned inner than each end in the width direction of the first inflated/deflated space. Thus, a cuff for a blood pressure monitor fabricated with ease and at low cost, exhibiting high pressing performance and high avascularization performance, and suitable for reduction of cuff width can be provided.

9 Claims, 9 Drawing Sheets

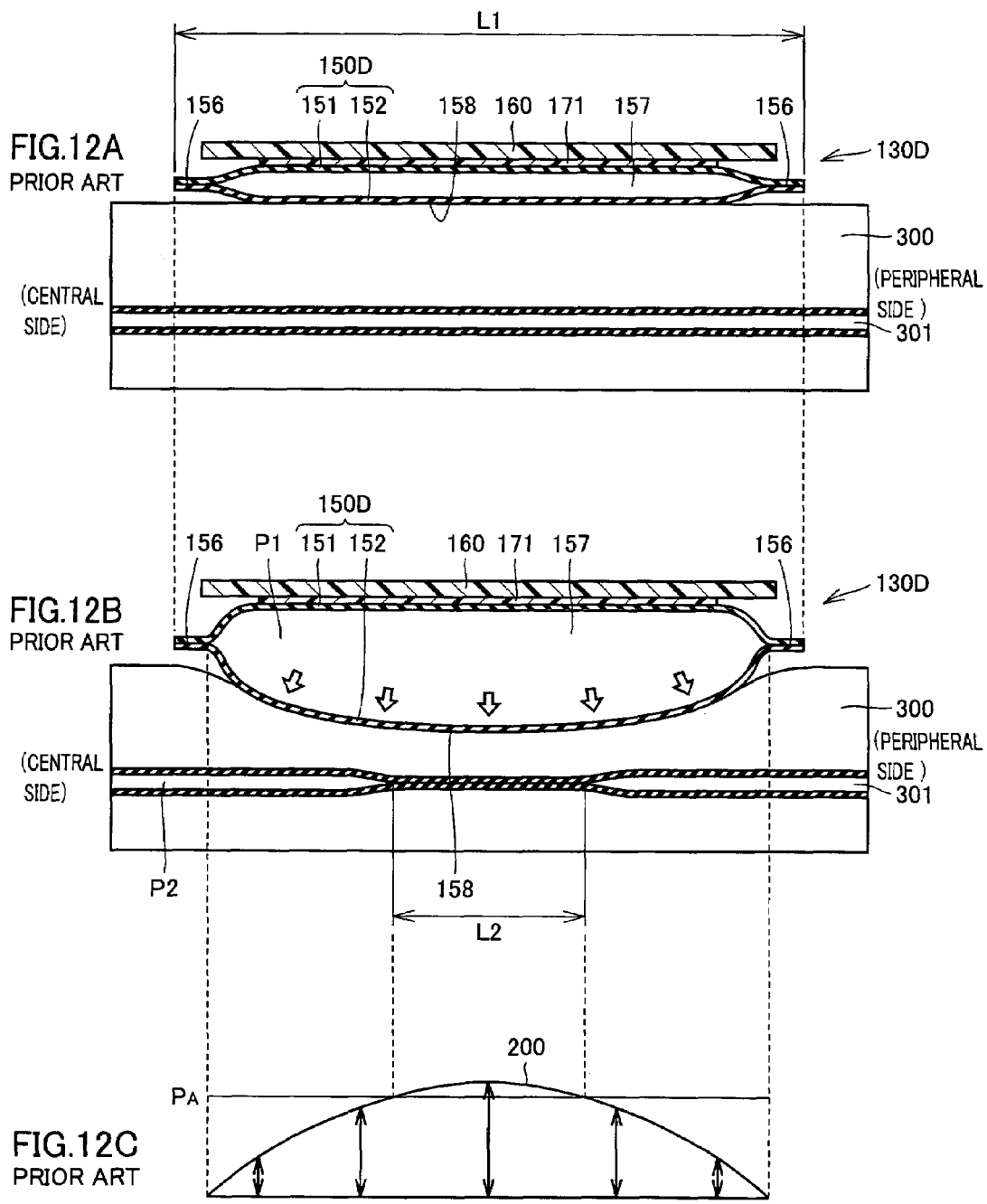

CUFF FOR BLOOD PRESSURE MONITOR AND BLOOD PRESSURE MONITOR HAVING THE SAME

BACKGROUND OF THE INVENTION

1. Field of the Invention

The present invention relates to a cuff for a blood pressure monitor provided with a fluid bag for avascularization of an artery by pressing a living body, and a blood pressure monitor having the cuff.

2. Description of the Background Art

To measure a blood pressure value, generally, a cuff provided with a fluid bag for pressing an artery located within a living body is wound around the body surface, and arterial pressure pulse waves caused in the artery by inflation/deflation of the fluid bag are detected to measure the blood pressure value. Here, the cuff refers to a band-shaped structure having a bladder, which can be wound around a part of a living body, for use in measurement of arterial pressure of an upper limb, a lower limb or the like by introducing fluid such as gas or liquid into the bladder. Thus, the cuff represents the concept including the fluid bag as well as members for winding the fluid bag around the living body. Particularly, the cuff wound around and fitted on a wrist or an upper arm is also called an arm band or a manchette.

Recently, blood pressure monitors are often used not only in medical treatment facilities such as hospitals but also in the households as an apparatus for checking the physical conditions day by day. As such, there are strong demands for improvement in handling of the blood pressure monitors, particularly for ease in fitting operation. To this end, downsizing of the cuff has been attempted. To downsize the cuff, it is necessary to narrow the cuff particularly in the width direction (i.e., direction parallel to the axial direction of the measurement site (e.g., wrist, upper arm or the like) to which the cuff is applied), for achievement of excellent fitting even for a person having an upper arm of short length, or for improved fitting to a wrist.

To narrow the width of the cuff for the blood pressure monitor, it is important to ensure that the artery is sufficiently pressed for avascularization. In the case of using a cuff for a blood pressure monitor having a large width, a long length in the axial direction of the measurement site covered by the cuff can be guaranteed, which enables sufficient pressing and avascularization of the artery. However, if the width of the cuff is narrowed, the length in the axial direction of the measurement site covered by the cuff becomes short, in which case it would be difficult to sufficiently press the artery for avascularization. This will be explained in detail in the following.

FIGS. 12A-12C are conceptual diagrams illustrating avascularization performance in the case where a cuff for a blood pressure monitor of Conventional Example 1 is used to press the artery inside the living body for avascularization. FIG. 12A is a schematic cross sectional view in the width direction of the cuff for a blood pressure monitor of Conventional Example 1, showing the state where the cuff is fitted on the living body. FIG. 12B is a schematic cross sectional view showing the state where the artery is pressed for avascularization using the cuff for a blood pressure monitor of Conventional Example 1. FIG. 12C shows pressure distribution over the surface of the living body when pressed with the cuff for a blood pressure monitor of Conventional Example 1. In FIGS. 12A and 12B, the cover body covering the air bag is not shown.

As shown in FIG. 12A, the cuff 130D for a blood pressure monitor of Conventional Example 1 includes an air bag 150D formed by laying two resin sheets 151 and 152 one on the other and melting and bonding their rims, and a curled elastic member 160 identified as an elastic member that is attached to an outer peripheral surface of air bag 150D using a double-faced tape 171 identified as an attaching member. Air bag 150D has an inflated/deflated space 157 therein, and has a bonded portion 156 on each end in the width direction that is formed by the above-described melting and bonding. In the fitted state of the cuff, air bag 150D is located between the surface of living body 300 and curled elastic member 160. Herein, the width of air bag 150D is represented as L1.

When a pressurized air is introduced into inflated/deflated space 157 to inflate air bag 150D, air bag 150D increases in size in the thickness direction, as shown in FIG. 12B, and its working face 158 pressing living body 300 expands in a balloon shape. With curled elastic member 160 secured, inflation of air bag 150D outwards, i.e., in the opposite direction from living body 300 is restricted, and air bag 150D is inflated only on the side of living body 300. As such, living body 300 is pressed by air bag 150D, and the artery 301 located under the skin of living body 300 is pressed for avascularization.

In order to completely occlude artery 301, it is required that the pressure applied by air bag 150D to the surface of living body 300 is not less than a prescribed level. That is, when the pressure on the surface of living body 300 required to completely occlude artery 301 is represented as $P_A$, artery 301 is occluded only in the region where the pressure distribution curve 200 on the body surface exceeds pressure $P_A$, as shown in FIG. 12C. Herein, the length or distance of a portion of artery 301 in its extending direction occluded by inflation of air bag 150D (hereinafter, referred to as "artery occluded distance") is represented as L2.

In the state where artery 301 is pressed for avascularization, a pressure P2 within artery 301 on its central side represents a blood pressure value. In the blood pressure monitor, a change of pressure P1 within air bag 150D is read as pressure P2 on the central side within artery 301, to calculate the blood pressure value. Thus, for accurate measurement of the blood pressure value, it is necessary to minimize the difference between pressure P2 within artery 301 and pressure P1 within air bag 150D to the greatest possible extent, for which it is critical to secure a sufficiently long length of artery occluded distance L2 described above.

With the configuration of air bag 150D arranged inside cuff 130D for a blood pressure monitor of Conventional Example 1, however, air bag 150D is inflated in the balloon shape, making it difficult to sufficiently guarantee artery occluded distance L2 with respect to width L1 of air bag 150D. This causes degradation of accuracy in measurement, which problem is particularly noticeable when width L1 of cuff 130D for a blood pressure monitor is decreased. Such degradation of measurement accuracy due to deterioration of avascularization-performance poses a very serious problem.

A cuff for a blood pressure monitor disclosed in Japanese Patent Laying-Open No. 02-107226 and a cuff for a blood pressure monitor disclosed in Japanese Patent Laying-Open No. 2001-224558, for example, are known as those directed to prevent degradation of avascularization performance in association with a decreased cuff width. In each of the cuffs for a blood pressure monitor disclosed in these publications, an air bag identified as a fluid bag arranged inside the cuff is provided with a gusset at each end in the width direction. When the air bag is inflated, the gussets expand to make the air bag inflated more uniformly in the width direction.

Particularly in the case where the configuration disclosed in Japanese Patent Laying-Open No. 2001-224558 is employed, artery occluded distance L2 of a very long length can be guaranteed with respect to the width of the air bag, thereby rendering this technique essential for reduction of the cuff width. Hereinafter, the cuff for a blood pressure monitor disclosed in Japanese Patent Laying-Open No. 2001-224558 will be explained as Conventional Example 2.

FIGS. 13A-13C are conceptual diagrams illustrating avascularization performance when using the cuff for a blood pressure monitor of Conventional Example 2 to press the artery inside the living body for avascularization. FIG. 13A is a schematic cross sectional view in the width direction of the cuff for a blood pressure monitor of Conventional Example 2, showing the state where the cuff is fitted on the living body. FIG. 13B is a schematic cross sectional view showing the state where the artery is pressed for avascularization using the cuff for a blood pressure monitor of Conventional Example 2. FIG. 13C shows pressure distribution over the surface of the living body when pressed with the cuff for a blood pressure monitor of Conventional Example 2. In FIGS. 13A and 13B, the cover body covering the air bag is not shown.

As shown in FIG. 13A, the cuff 130E for a blood pressure monitor of Conventional Example 2 includes an air bag 150E and a curled elastic member 160. Air bag 150E has a bag member formed by laying two resin sheets 151 and 152 one on the other and melting and bonding their rims, and another bag member formed by laying two resin sheets 153 and 154 one on the other and melting and bonding their rims, which bag members are laid one on the other and melted and bonded together to form air bag 150E. Curled elastic member 160 identified as an elastic member is attached to an outer periphery surface of air bag 150E using a double-faced tape 171 as an attaching member. Air bag 150E has two layers of inflated/deflated spaces 157a, 157b therein, which are in communication with each other via a communication hole 159. Bonded portions 156a1, 156a2, formed by the above-described melting and bonding, are located at each end in the width direction of air bag 150E. In the fitted state of the cuff, air bag 150E is arranged between the surface of living body 300 and curled elastic member 160.

When a pressurized air is introduced into inflated/deflated spaces 157a, 157b to inflate air bag 150E, air bag 150E increases in size in the thickness direction, as shown in FIG. 13B. Since the gussets are provided at the respective ends in the width direction of air bag 150E, they expand in the thickness direction of air bag 150E, whereby a working face 158 of air bag 150E pressing living body 300 expands approximately flatly. As such, the both ends in the width direction of air bag 150E and their vicinities expand similarly to the central portion in the width direction of air bag 150E, ensuring more uniform pressing of artery 301 under the skin of living body 300.

As described above, with the configuration of air bag 150E contained in cuff 130E for a blood pressure monitor of Conventional Example 2, working face 158 of air bag 150E pressing the living body expands approximately flatly. Thus, compared to the case of air bag 150D contained in cuff 130D for a blood pressure monitor of Conventional Example 1, artery occluded distance L2 can be secured longer with respect to width L1 of the air bag. As a result, it is possible to measure a blood pressure value with accuracy even if the cuff width is reduced.

Although the structure of air bag 150E contained in cuff 130E for a blood pressure monitor of Conventional Example 2 is suitable for accurate measurement of the blood pressure value, it requires a large number of resin sheets, and also requires joining of the resin sheets in several steps. As such, the production is complicated, and the cost is high.

SUMMARY OF THE INVENTION

An object of the present invention is to provide a cuff for a blood pressure monitor that can be fabricated with ease and at low cost, that has favorable pressing performance and avascularization performance, and that is suitable for reduction of a cuff width, and to provide a blood pressure monitor provided with the cuff.

A cuff for a blood pressure monitor according to the present invention has a fluid bag inflated and deflated as a fluid comes in and out, which increases in size in a thickness direction when inflated and decreases in size in the thickness direction when deflated. The fluid bag includes a first bag member located on an outer side in the thickness direction in the state where the cuff for a blood pressure monitor is fitted on a living body and having a first inflated/deflated space therein, and a second bag member located on an inner side in the thickness direction in the state where the cuff for a blood pressure monitor is fitted on the living body and having a second inflated/deflated space therein. The second bag member is formed by laying a single-layer sheet-shaped member on a surface of the first bag member on the living body side and joining its rim to the living body-side surface. A joined portion of the first bag member with the single-layer sheet-shaped member is positioned inner than each end in a width direction of the first inflated/deflated space.

With this configuration, at the time when the fluid bag is inflated, the single-layer sheet-shaped member constituting a part of the second bag member expands with the joined portion provided inner than each end in the width direction of the first inflated/deflated space as a base point. This ensures sufficient inflation of the fluid bag in the thickness direction. As such, it is possible to press the living body strongly and uniformly over the wide range of the living body, and thus, to secure a long length of the artery occluded distance with respect to the width of the fluid bag. Accordingly, it is possible to provide a cuff for a blood pressure monitor having high avascularization performance with a very simple configuration, which is suitable for decreasing the cuff width.

In the cuff for a blood pressure monitor based on the invention described above, it is preferable that the single-layer sheet-shaped member constituting a part of the second bag member is more elastic than a member forming the living body-side surface of the first bag member.

With this configuration, the single-layer sheet-shaped member constituting a part of the second bag member is allowed to inflate more flatly in the width direction of the fluid bag, so that the artery occluded distance of still longer length can be guaranteed, which leads to accurate measurement of the blood pressure value.

In the cuff for a blood pressure monitor based on the invention described above, it is preferable that a material of the single-layer sheet-shaped member constituting a part of the second bag member is soft polyvinyl chloride, copolymer of ethylene-vinyl acetate, polyurethane, or thermoplastic elastomer olefin.

When the sheet-shaped member of such material is employed, the fluid bag becomes superior in elasticity.

In the cuff for a blood pressure monitor based on the invention described above, it is preferable that the single-layer sheet-shaped member constituting a part of the second bag member and a member forming the living body-side surface of the first bag member are made of a same material.

When the first bag member and the second bag member are formed using the sheet-shaped members of the same material, it is possible to join them by melting and bonding, which allows fabrication of the cuff for a blood pressure monitor of high performance at low cost.

In the cuff for a blood pressure monitor based on the invention described above, it is preferable that the single-layer sheet-shaped member constituting a part of the second bag member has a thickness smaller than a thickness of a member forming the living body-side surface of the first bag member.

With this configuration, it is possible to make the single-layer sheet-shaped member constituting a part of the second bag member superior in elasticity to the other sheet-shaped member(s), even if the sheet-shaped members of the same material are used to form the first and second bag members.

In the cuff for a blood pressure monitor based on the invention described above, it is preferable that the first bag member is formed by laying a plurality of sheet-shaped members one on another and joining their rims together.

With this configuration, it is possible to fabricate a cuff for a blood pressure monitor in a relatively simple manner.

Further, in the cuff for a blood pressure monitor based on the invention described above, it is preferable that the first inflated/deflated space and the second inflated/deflated space are in communication with each other.

A blood pressure monitor according to the present invention includes: one of the cuffs for a blood pressure monitor described above; an inflating/deflating portion for inflating and deflating the fluid bag; a pressure detecting portion for detecting a pressure within the fluid bag; and a blood pressure value calculating portion for calculating a blood pressure value based on pressure information detected by the pressure detecting portion.

With this configuration, accurate measurement of the blood pressure value is ensured even if the cuff width is reduced. Thus, a blood pressure monitor of high performance that is easy to fit can be obtained.

According to the present invention, it is possible to fabricate a cuff for a blood pressure monitor having high pressing performance and high avascularization performance, as well as a blood pressure monitor having the cuff, with ease and at low cost. Accordingly, the cuff for a blood pressure monitor suitable for decreasing the cuff width, and the blood pressure monitor provided with the same, can be obtained.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 12A is a schematic cross sectional view in a width direction of a cuff for a blood pressure monitor according to Conventional Example 1, showing the state where the cuff is fitted on a living body.

FIG. 12B is a schematic cross sectional view in the width direction of the cuff for a blood pressure monitor according to Conventional Example 1, showing the state where an artery is pressed for avascularization using the cuff.

FIG. 12C shows pressure distribution on a surface of the living body when pressed by the cuff for a blood pressure monitor according to Conventional Example 1.

DESCRIPTION OF THE PREFERRED EMBODIMENTS

Hereinafter, an embodiment of the present invention will be described in detail with reference to the drawings. In the embodiment described below, a wrist blood pressure monitor will be explained by way of example.

Figure 1:
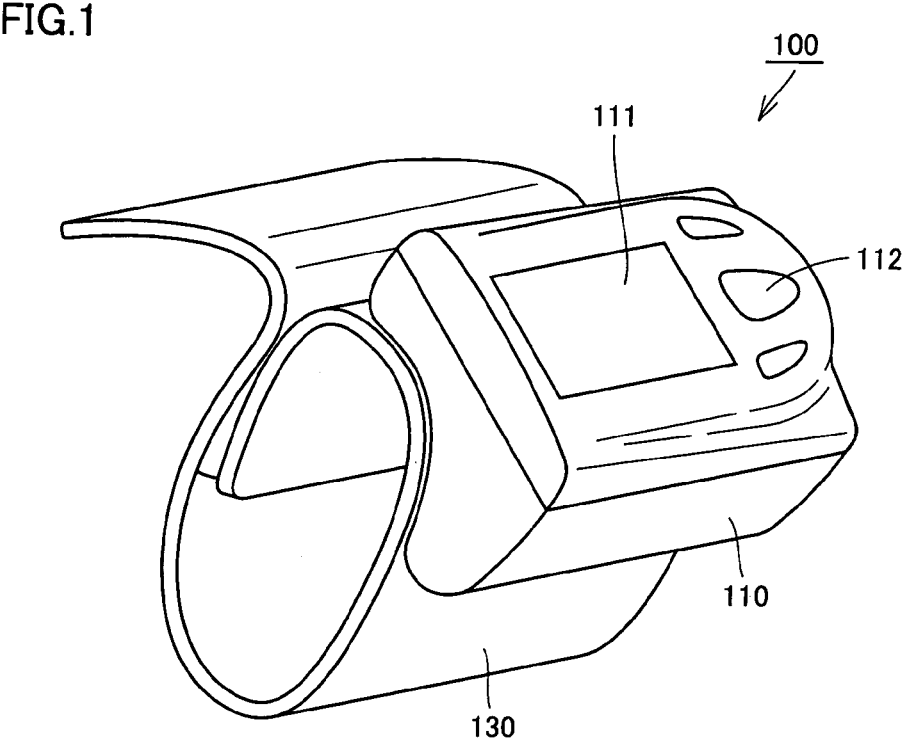
FIG. 1 is a perspective view of a blood pressure monitor according to an embodiment of the present invention.

FIG. 1 is a perspective view of a blood pressure monitor according to the present embodiment. As shown in FIG. 1, the blood pressure monitor 100 of the present embodiment includes a main body 110 and a cuff 130. A display portion 111 and a manipulation portion 112 are arranged on the surface of main body 110. Cuff 130 is attached to main body 110.

Figure 2:
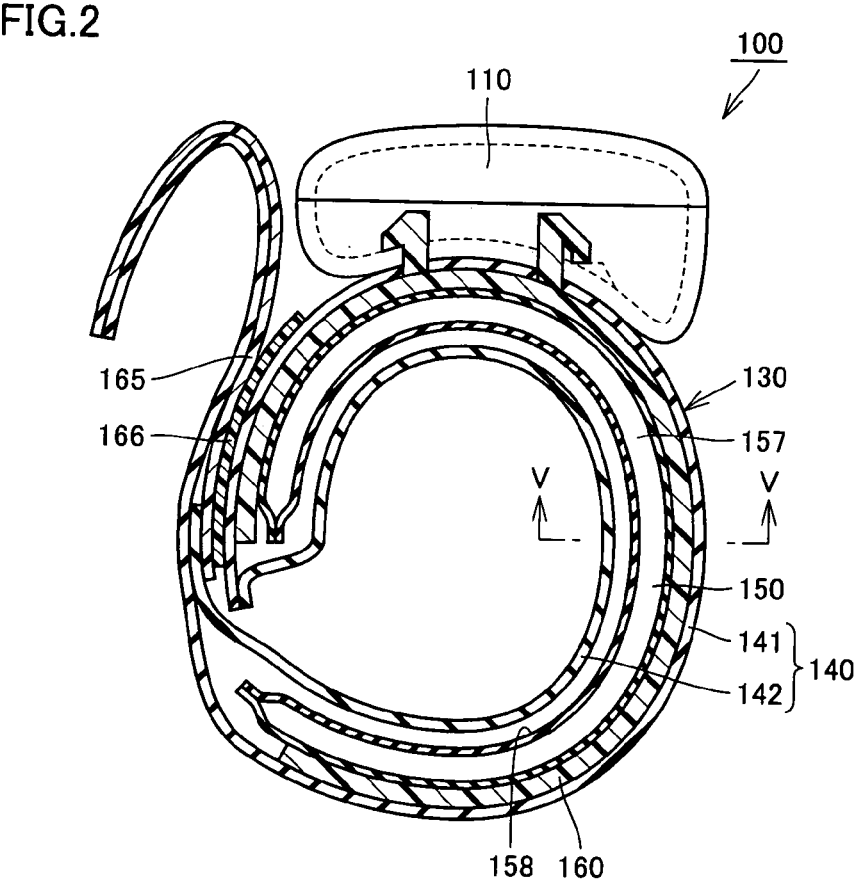
FIG. 2 is a vertical cross sectional view showing an inner structure of a cuff for the blood pressure monitor according to the embodiment of the present invention.

FIG. 2 is a vertical cross sectional view showing an inner structure of the cuff for the blood pressure monitor shown in FIG. 1. As shown in FIG. 2, cuff 130 for the blood pressure monitor of the present embodiment primarily includes a cover member 140 of a bag shape that is made of cloth or the like, an air bag 150 identified as a fluid bag that is arranged inside cover member 140, and a curled elastic member 160 that is arranged inside cover member 140 on an outer side of air bag 150 in the fitted state of the cuff. Curled elastic member 160 is elastic and curved to temporarily mount the cuff on the wrist. Cover member 140, air bag 150 and curled elastic member 160 extend with their longitudinal direction corresponding to the winding direction of cuff 130.

Cover member 140 has an inner cover 142 made of cloth or the like superior in elasticity and positioned on the inner side in the fitted state, and an outer cover 141 made of cloth or the like inferior in elasticity and positioned on the outer side than inner cover 142. Inner cover 142 and outer cover 141 are laid one on the other and their rims are sewn up to form a bag shape. On one end in the longitudinal direction of cover member 140, a velcro fastener 165 is provided on the inner peripheral surface. On the other end in the longitudinal direction of cover member 140, a velcro fastener 166 for engagement with velcro fastener 165 is attached to the outer peripheral surface. Velcro fasteners 165, 166 are members for securing blood pressure monitor 100 on the measurement site of the wrist in a stable manner when cuff 130 is mounted on the wrist.

Air bag 150 is made of a member of bag shape that is formed using resin sheets identified as sheet-shaped members, and has an inflated/deflated space 157 therein. An inner peripheral surface of air bag 150 serves as a working face 158 for pressing the wrist. Inflated/deflated space 157 is connected via a tube 120 to an air system 121 for blood pressure measurement of main body 110, which will be described later (see FIG. 3). The detailed structure of air bag 150 will be described later.

As the material for the resin sheets constituting air bag 150, any material can be used as long as it exhibits excellent elasticity and prevents leakage of the air from inflated/deflated space 157 after melting and bonding. From these standpoints, optimal materials for the resin sheets include copolymer of ethylene-vinyl acetate (EVA), soft polyvinyl chloride (PVC), polyurethane (PU), thermoplastic elastomer olefin (TPE-O), crude rubber, and the like.

On the outer side of air bag 150, curled elastic member 160 identified as an elastic member is arranged, which is wound in an annular shape and elastically deformable in a radial direction. Curled elastic member 160 is attached to the outer surface of the outer wall portion of air bag 150 using an attaching member such as a double-faced tape (not shown). Curled elastic member 160 is configured to maintain its own annular shape, and serves to fit air bag 150 exactly on the living body in the mounted state of the cuff. Curled elastic member 160 is made of a resin member of polypropylene or the like, so as to exert sufficient elastic force.

Figure 3:
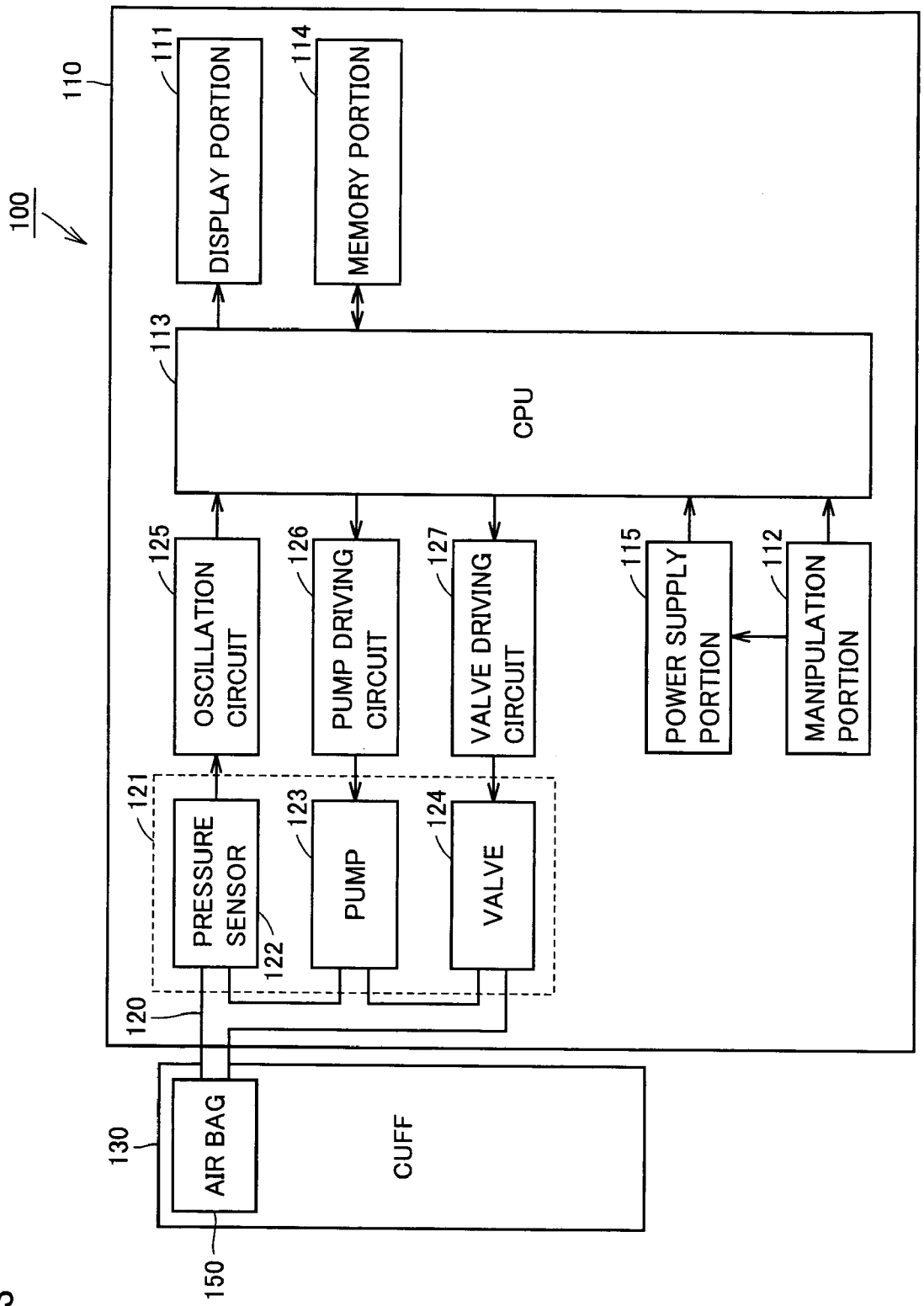
FIG. 3 is a block diagram showing a configuration of the blood pressure monitor according to the embodiment of the present invention.

FIG. 3 is a block diagram showing a configuration of the blood pressure monitor according to the present embodiment. As shown in FIG. 3, main body 110 includes an air system 121 for blood pressure measurement for supplying and evacuating the air to and from air bag 150 via a tube 120, and an oscillation circuit 125, a pump driving circuit 126 and a valve driving circuit 127 which are provided in association with air system 121 for blood pressure measurement. These components function as an inflating/deflating portion for inflating and deflating air bag 150.

Main body 110 further includes a CPU (Central Processing Unit) 113 for controlling and monitoring the respective portions in a centralized manner, a memory portion 114 for storing a program for causing CPU 113 to conduct a prescribed operation and various information including blood pressure values measured, a display portion 111 for displaying the information including a blood pressure measurement result, a manipulation portion 112 manipulated for inputting various instructions for measurement, and a power supply portion 115 for supplying electric power to CPU 113 by an instruction of power ON from manipulation portion 112. CPU 113 serves as a blood pressure value calculating portion for calculating a blood pressure value.

Air system 121 for blood pressure measurement has a pressure sensor 122 having an output value changed in accordance with the pressure within air bag 150 (hereinafter, referred to as "cuff pressure"), a pump 123 for supplying the air to air bag 150, and a valve 124 that is opened or closed to evacuate the air from or seal the air in air bag 150. Pressure sensor 122 serves as a pressure detecting portion for detecting the cuff pressure. Oscillation circuit 125 outputs to CPU 113 a signal of oscillation frequency corresponding to the output value of pressure sensor 122. Pump driving circuit 126 controls driving of pump 123 based on a control signal supplied from CPU 113. Valve driving circuit 127 controls opening/closing of valve 124 based on a control signal supplied from CPU 113.

Figure 4:
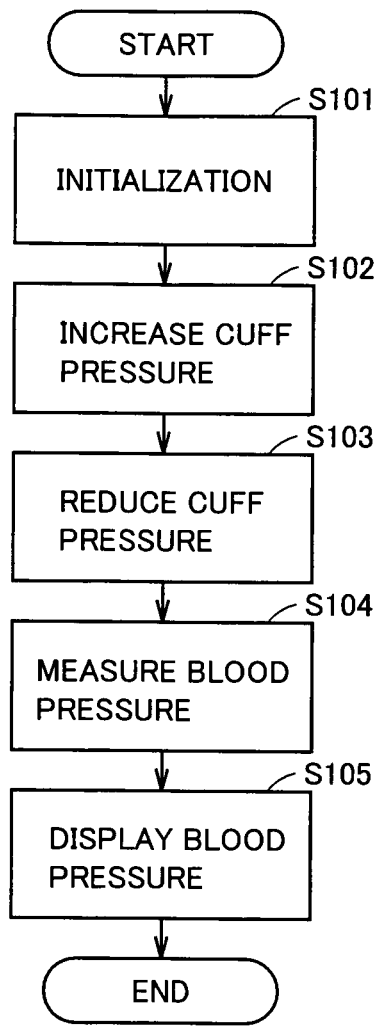
FIG. 4 is a flowchart illustrating a flow of blood pressure measuring process of the blood pressure monitor according to the embodiment of the present invention.

FIG. 4 is a flowchart illustrating the process flow of blood pressure measurement by the blood pressure monitor according to the present embodiment. The program according to this flowchart is prestored in memory portion 114, and the blood pressure measuring process is carried out as CPU 113 reads out this program from memory portion 114 and executes the same.

As shown in FIG. 4, when a subject manipulates a manipulation button on manipulation portion 112 to turn the power ON, blood pressure monitor 100 is initialized (step S101). When it becomes a measurable state, CPU 113 starts driving of pump 123 to gradually increase the cuff pressure of air bag 150 (step S102). During the process of gradually increasing the pressure, when the cuff pressure reaches a prescribed level for measuring the blood pressure, CPU 113 stops pump 123, and gradually opens the closed valve 124 to evacuate the air from air bag 150, so as to gradually reduce the cuff pressure (step S103). In the present embodiment, the blood pressure is measured during the process of gradually decreasing the cuff pressure.

Next, CPU 113 calculates the blood pressure (systolic blood pressure, diastolic blood pressure) in a known manner (step S104). Specifically, during the process where the cuff pressure is gradually decreased, CPU 113 extracts pulse wave information based on the oscillation frequency obtained from oscillation circuit 125. It then calculates the blood pressure value from the pulse wave information extracted. The blood pressure value obtained in step S104 is displayed on display portion 111 (step S105). Although the measurement method described above is based on a so-called "decreasing-pressure measurement method" where the pulse waves are detected while the air bag is being decreased in pressure, it is of course possible to employ a so-called "increasing-pressure measurement method" where the pulse waves are detected while the air bag is being increased in pressure.

Blood pressure monitor 110 and cuff 130 for a blood pressure monitor of the present embodiment are characterized by the structure of air bag 150 arranged inside cuff 130 for a blood pressure monitor. Hereinafter, the structure of air bag 150 will be described in detail for various examples, with reference to the drawings.

EXAMPLE 1

Figure 5:
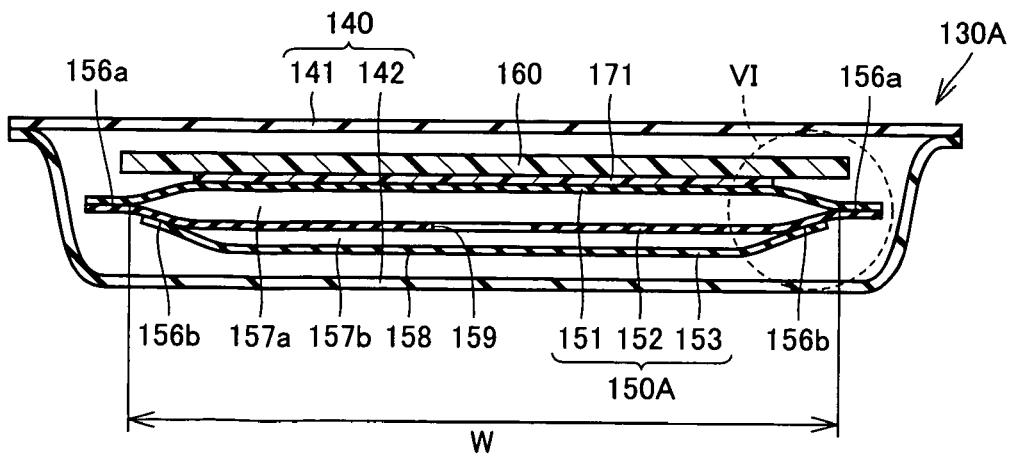
FIG. 5 is a schematic cross sectional view of a cuff for a blood pressure monitor according to Example 1 based on the embodiment of the present invention, taken along the line V-V in FIG. 2.
Figure 6:
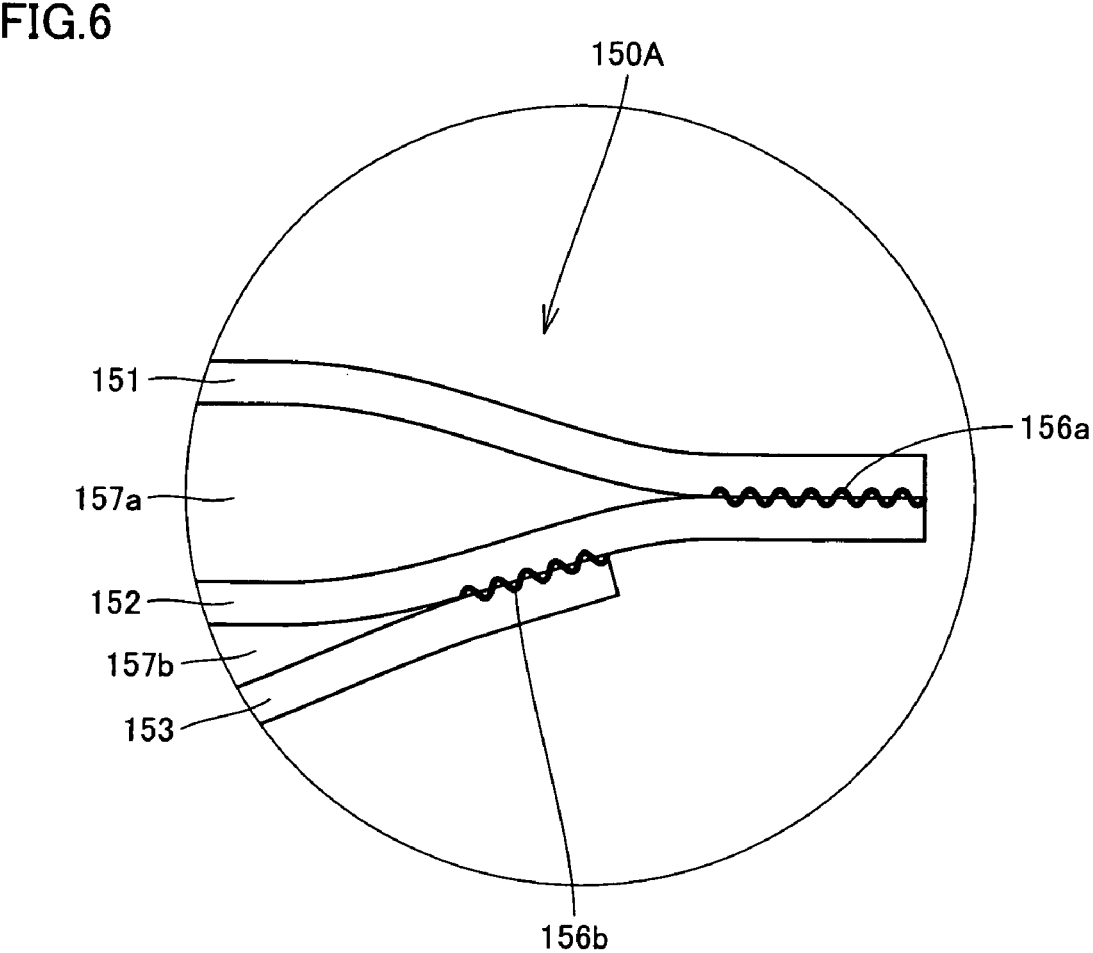
FIG. 6 is an enlarged view of the region VI shown in FIG. 5.

FIG. 5 is a schematic cross sectional view of a cuff for a blood pressure monitor according to Example 1 based on the present embodiment, taken along the line V-V shown in FIG. 2. FIG. 6 is an enlarged view of a region VI shown in FIG. 5.

As shown in FIG. 5, the cuff 130A for a blood pressure monitor of the present example includes an air bag 150A identified as a fluid bag and a curled elastic member 160 identified as an elastic member, which are arranged inside a cover member 140 formed of an inner cover 142 and an outer cover 141. Curled elastic member 160 is attached to an outer peripheral surface of air bag 150A via a double-faced tape 171 identified as an attaching member.

Air bag 150A is formed into a bag shape using three resin sheets 151, 152 and 153. Air bag 150A includes a first bag member positioned on the outer side in the thickness direction of air bag 150A in the state where cuff 130A for a blood pressure monitor is mounted on the wrist, and a second bag member positioned on the inner side in the thickness direction of air bag 150A in the state where cuff 130A is mounted on the wrist. The first bag member is formed of two resin sheets 151 and 152, and has a first inflated/deflated space 157a therein. The second bag member is formed of two resin sheets 152 and 153, and has a second inflated/deflated space 157b therein. First and second inflated/deflated spaces 157a and 157b are in communication with each other via a communication hole 159 provided at a prescribed position of resin sheet 152.

Resin sheet 153 constitutes an inner wall portion of air bag 150A. Resin sheet 151 constitutes an outer wall portion of air bag 150A. A surface on the wrist side of the inner wall portion of air bag 150A functions as a working-face 158 for pressing the wrist.

Figure 13A:
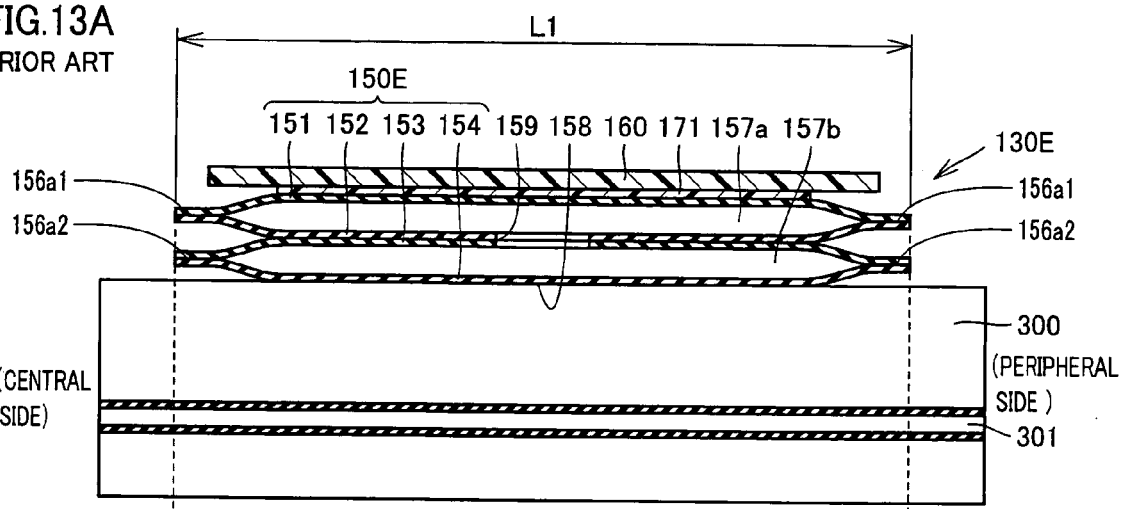
FIG. 13A is a schematic cross sectional view in a width direction of a cuff for a blood pressure monitor according to Conventional Example 2, showing the state where the cuff is fitted on a living body.
Figure 13B:
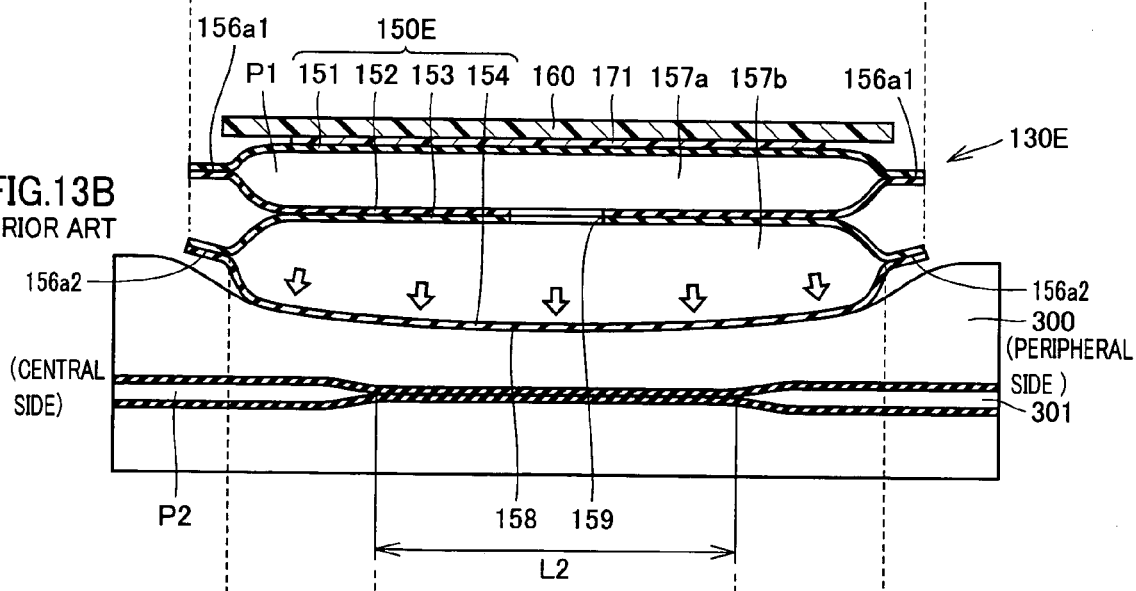
FIG. 13B is a schematic cross sectional view in the width direction of the cuff for a blood pressure monitor according to Conventional Example 2, showing the state where an artery is pressed for avascularization using the cuff.
Figure 13C:
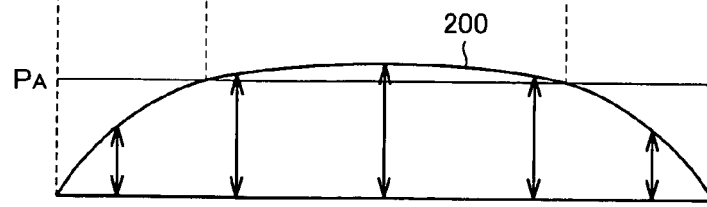
FIG. 13C shows pressure distribution on a surface of the living body when pressed by the cuff for a blood pressure monitor according to Conventional Example 2.

Air bag 150A of the above-described configuration is fabricated, e.g., in the following manner. Two resin sheets 151, 152 of an approximately rectangular shape in two dimensions are laid one on the other and their rims are melted and bonded to form the first bag member. Further, resin sheet 153 of an approximately rectangular shape but slightly narrower in width is laid on the first bag member, and the rim of resin sheet 153 is melted and bonded to a prescribed position on the outer surface of resin sheet 152 of the first bag member, to thereby form air bag 150A. Thus, compared to air bag 150E (see FIGS. 13A-13C) contained in cuff 130E for a blood pressure monitor of Conventional Example 2 described above, the air bag having two-layers of stacked inflated/deflated spaces can be formed using a smaller number of resin sheets. With the decrease in number of resin sheets, the number of melted and bonded portions also decreases. Accordingly, air bag 150A of the present example can be fabricated more easily and less expensively than air bag 150E of Conventional Example 2.

Two resin sheets 151 and 152 forming the first bag member having first inflated/deflated space 157a therein are joined together by stacking them and melting and boding their rims. Thus, as shown in FIG. 6, a bonded portion 156a is located at each end in the width direction of air bag 150A. By comparison, a bonded portion 156b that is the joined portion of two resin sheets 152 and 153 forming the second bag member having second inflated/deflated space 157b therein is provided inner than each end in the width direction of first inflated/deflated space 157a formed inside the first bag member. More specifically, bonded portion 156b of resin sheets 152 and 153 is positioned closer to the central portion than each end of a region W (see FIG. 5) where first inflated/deflated space 157a is located. This means that bonded portion 156b of resin sheets 152 and 153 is located still inner than the inner end of bonded portion 156a of resin sheets 151 and 152. Preferably, at each end of resin sheet 152, bonded portion 156a and bonded portion 156b are spaced apart from each other by a prescribed distance. Herein, as the prescribed distance, more than about 5% and less than about 25% of the width (shown by W in FIG. 5) of inflated/deflated space 157a of the first bag member is suitable.

With cuff 130A for a blood pressure monitor thus configured, high pressing performance and high avascularization performance are obtained. This will be explained in detail in the following.

Figure 7:
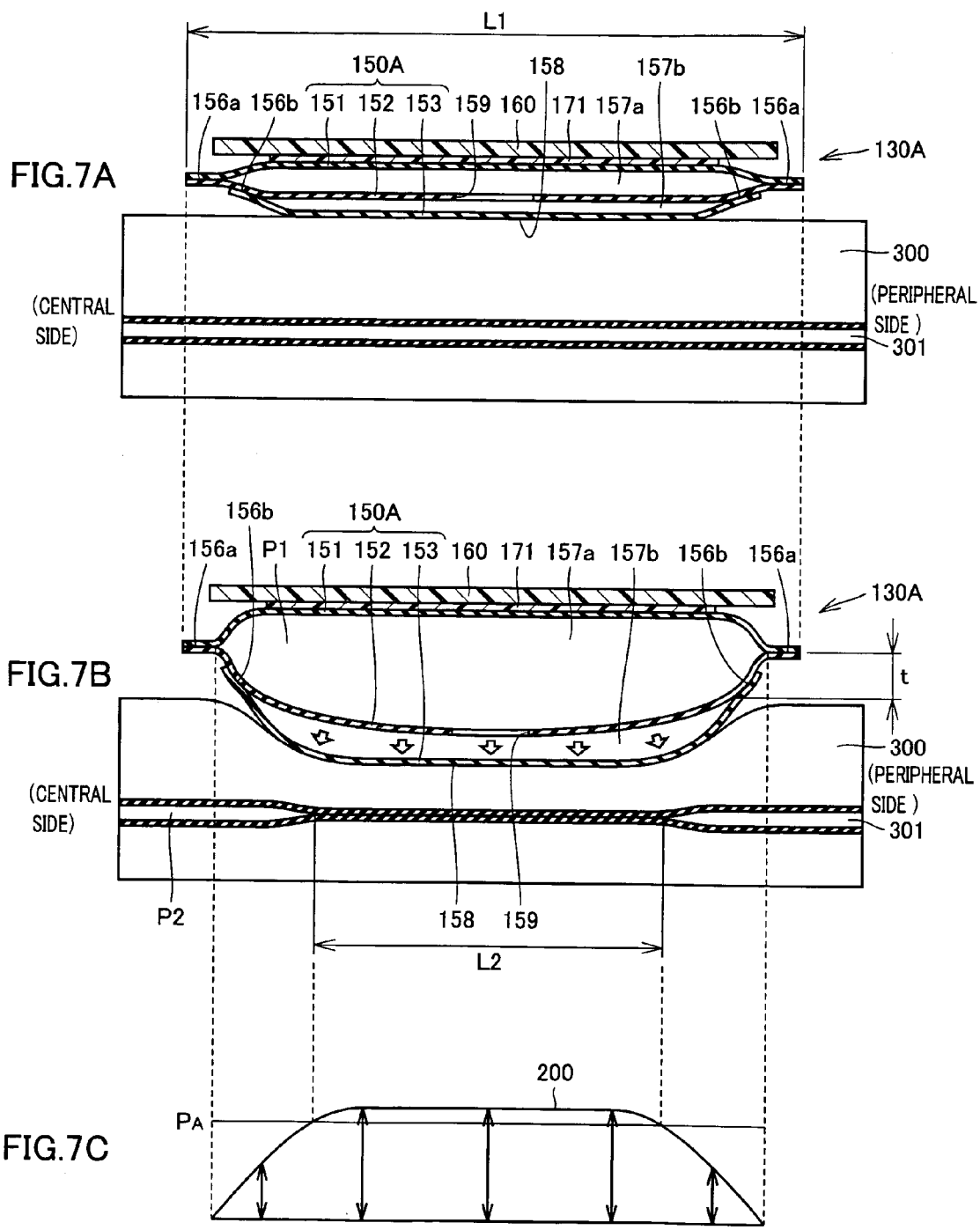
FIG. 7A is a schematic cross sectional view in a width direction of the cuff for a blood pressure monitor according to Example 1 based on the embodiment of the present invention, showing the state where the cuff is fitted on a living body.
FIG. 7B is a schematic cross sectional view in the width direction of the cuff for a blood pressure monitor according to Example 1 based on the embodiment of the present invention, showing the state where an artery is pressed for avascularization using the cuff.
FIG. 7C shows pressure distribution on a surface of the living body when pressed by the cuff for a blood pressure monitor according to Example 1 based on the embodiment of the present invention.

FIGS. 7A-7C are conceptual diagrams illustrating avascularization performance in the case where the cuff for a blood pressure monitor of the present example is used to press the artery inside the living body for avascularization. FIG. 7A is a schematic cross sectional view in the width direction of the cuff for a blood pressure monitor of the present example, showing the state where the cuff is fitted on the living body. FIG. 7B is a schematic cross sectional view showing the state where the artery is pressed for avascularization using the cuff for a blood pressure monitor of the present example. FIG. 7C shows pressure distribution on the surface of the living body when pressed with the cuff for a blood pressure monitor of the present example. In FIGS. 7A and 7B, the cover body covering the air bag is not shown.

As shown in FIG. 7A, in the state where cuff 130A for a blood pressure monitor is applied to living body 300, air bag 150A is arranged between the surface of living body 300 and curled elastic member 160. At this time, on the surface of living body 300, the first bag member of air bag 150A is located on the outer side in the direction crossing the axial direction of living body 300, and the second bag member is located on the inner side.

When a pressurized air is introduced into inflated/deflated space 157a to inflate air bag 150A, air bag 150A increases in size in the thickness direction, as shown in FIG. 7B. At this time, resin sheet 152 forming a part of the first bag member expands in a balloon shape toward living body 300. Since the pressurized air flows from first inflated/deflated space 157a to second inflated/deflated space 157b via communication hole 159, resin sheet 153 forming a part of the second bag member also expands in a balloon shape toward living body 300.

Here, in air bag 150A contained in cuff 130A for a blood pressure monitor of the present example, bonded portion 156b of the first bag member with the second bag member is located inner than each end in the width direction of inflated/deflated space 157a formed in the first bag member by a prescribed distance. Thus, resin sheet 153 forming a part of the second bag member expands with this bonded portion 156b as a base point. As such, stroke t of bonded portion 156b toward the living body occurs along with inflation of the first bag member as shown in FIG. 7B, and thus, compared to air bag 150D (see FIGS. 12A-12C) contained in cuff 130D for a blood pressure monitor of Conventional Example 1, a further increase in size of the air bag in the direction of the living body is allowed upon inflation of the second bag member.

Accordingly, pressure distribution on the surface of living body 300 becomes uniform in the axial direction of living body 300, as shown in FIG. 7C, so that it is possible to uniformly and strongly press the living body over a wide area of the wrist on which cuff 130A for a blood pressure monitor is mounted. This ensures a long length of artery occluded distance L2 with respect to width L1 of air bag 150A, which leads to improvement of accuracy in measurement of the blood pressure value.

In air bag 150A contained in cuff 130A for a blood pressure monitor of the present example, it is preferable that resin sheet 153 forming a part of the second bag member is superior in elasticity to resin sheets 151, 152 forming the first bag member. By providing resin sheet 153 more elastic than other resin sheets 151 and 152, the pressurized air is distributed sufficiently to reach the both ends in the width direction of the second bag member, which makes it possible to press living body 300 more flatly. To make resin sheet 153 forming a part of the second bag member more elastic than resin sheets 151 and 152 forming the first bag member, three resin sheets 151, 152 and 153 may be made of the same material and resin sheet 153 forming a part of the second bag member may be made thinner than other resin sheets 151 and 152. Alternatively, resin sheet 153 forming a part of the second bag member may be formed of a material that is more elastic than the material of other resin sheets 151 and 152.

As described above, with the configuration of air bag 150A contained in cuff 130A for a blood pressure monitor according to the present example, it is possible to provide a cuff for a blood pressure monitor implementing high pressing performance and high avascularization performance with a simple configuration. This cuff for a blood pressure monitor is suitable for reduction of the cuff width. Accordingly, a blood pressure monitor of high performance and of which fitting operation is simple can be provided.

EXAMPLE 2

Figure 8:
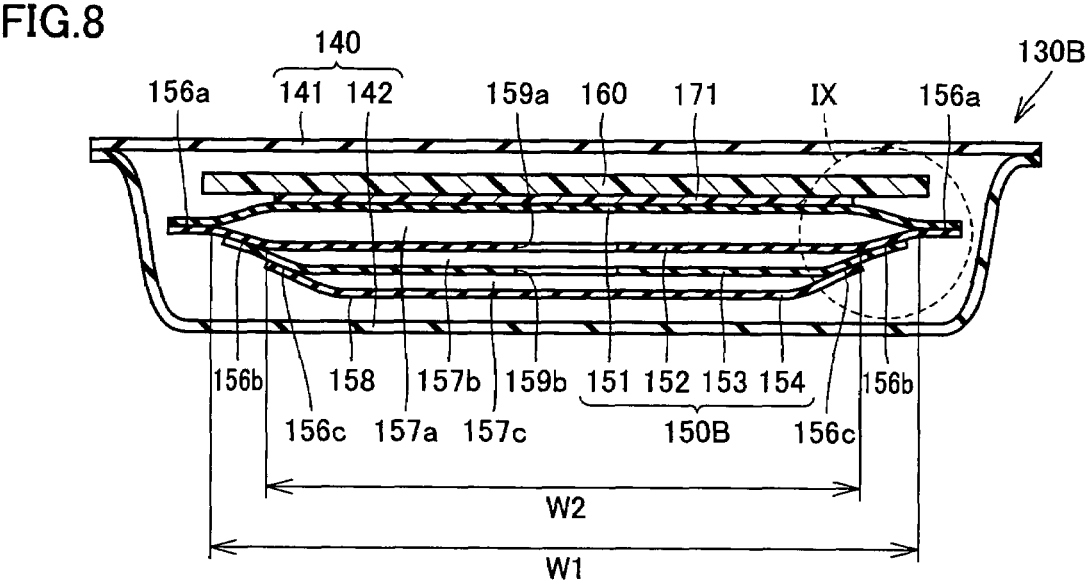
FIG. 8 is a schematic cross sectional view of a cuff for a blood pressure monitor according to Example 2 based on the embodiment of the present invention.
Figure 9:
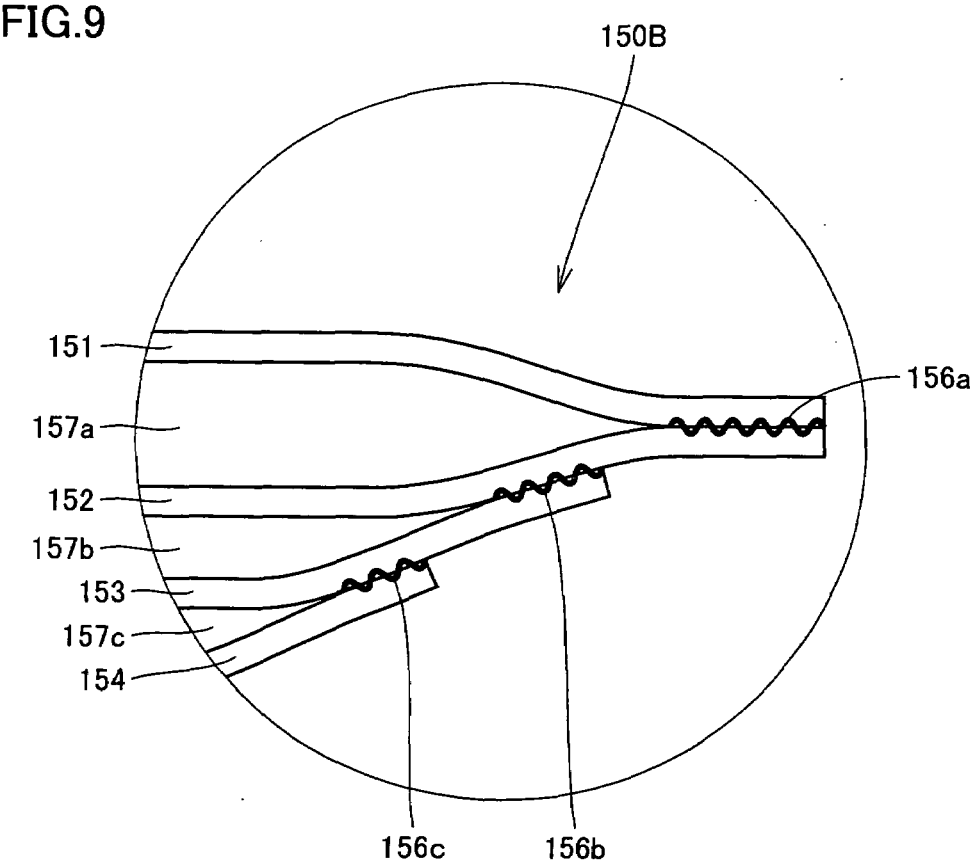
FIG. 9 is an enlarged view of the region IX shown in FIG. 8.

FIG. 8 is a schematic cross sectional view of a cuff for a blood pressure monitor according to Example 2 based on the present embodiment. FIG. 9 is an enlarged view of a region IX shown in FIG. 8. In the following, the portions different from those of cuff 130A for a blood pressure monitor of Example 1 will be described, while description of the similar portions will not be repeated.

As shown in FIG. 8, the air bag 150B contained in the cuff 130B for a blood pressure monitor according to the present example has a configuration where a single-layer resin sheet 154 is additionally provided on the outer surface on the living body side of air bag 150A contained in cuff 130A for a blood pressure monitor of Example 1 described above.

Air bag 150B includes a first bag member located on the outer side in the thickness direction of air bag 150B in the state where cuff 130B for a blood pressure monitor is mounted on the wrist, and a second bag member located on the inner side in the thickness direction of air bag 150B in the state where cuff 130B is mounted on the wrist. The first bag member is formed of three resin sheets 151, 152 and 153, and has first inflated/deflated spaces 157a, 157b therein. First inflated/deflated spaces 157a and 157b partitioned by resin sheet 152 are in communication with each other via a communication hole 159a formed at a prescribed position of resin sheet 152. The second bag member is formed of two resin sheets 153 and 154, and has a second inflated/deflated space 157c therein. First inflated/deflated space 157b located on the living body side is in communication with second inflated/deflated space 157c via a communication hole 159b provided at a prescribed position of resin sheet 153.

Resin sheet 154 constitutes an inner wall portion of air bag 150B. Resin sheet 151 constitutes an outer wall portion of air bag 150B. A surface on the wrist side of the inner wall portion of air bag 150B functions as a working face 158 for pressing the wrist.

Air bag 150B having the above-described configuration is fabricated, e.g., in the following manner. A resin sheet 154 of an approximately rectangular shape in two dimensions and having a narrow width is laid on air bag 150A shown in Example 1 above, and the rim of resin sheet 154 is melted and bonded to a prescribed position on the outer surface of resin sheet 153 of the first bag member.

In air bag 150B contained in cuff 130B for a blood pressure monitor of the present example, as shown in FIG. 9, a bonded portion 156c that is a joined portion of two resin sheets 153 and 154 forming the second bag member and having second inflated/deflated space 157c therein is located inner than each end in the width direction of first inflated/deflated spaces 157a and 157b formed inside the first bag member. More specifically, bonded portion 156c of resin sheets 153 and 154 is provided closer to the central portion than each end of a region W1 (see FIG. 8) where first inflated/deflated space 157a is located, and is provided still closer to the central portion than each end of a region W2 (see FIG. 8) where first inflated/deflated space 157b is located. This enables resin sheet 154 forming a part of the second bag member to expand with this bonded portion 156c as a basic point, and accordingly, the effect equal to or superior to the effect explained in Example 1 above can be obtained.

EXAMPLE 3

Figure 10:
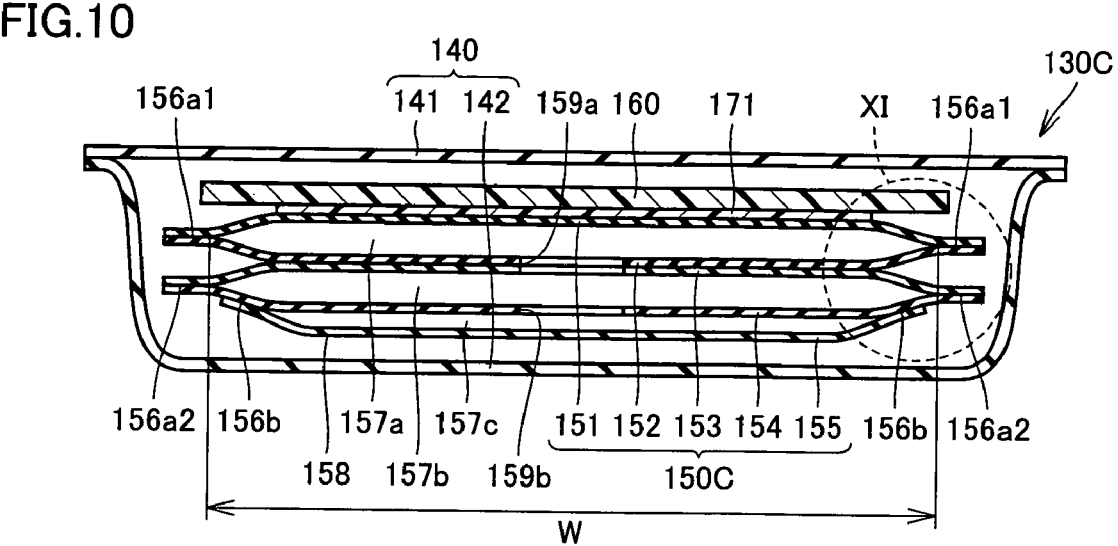
FIG. 10 is a schematic cross sectional view of a cuff for a blood pressure monitor according to Example 3 based on the embodiment of the present invention.
Figure 11:
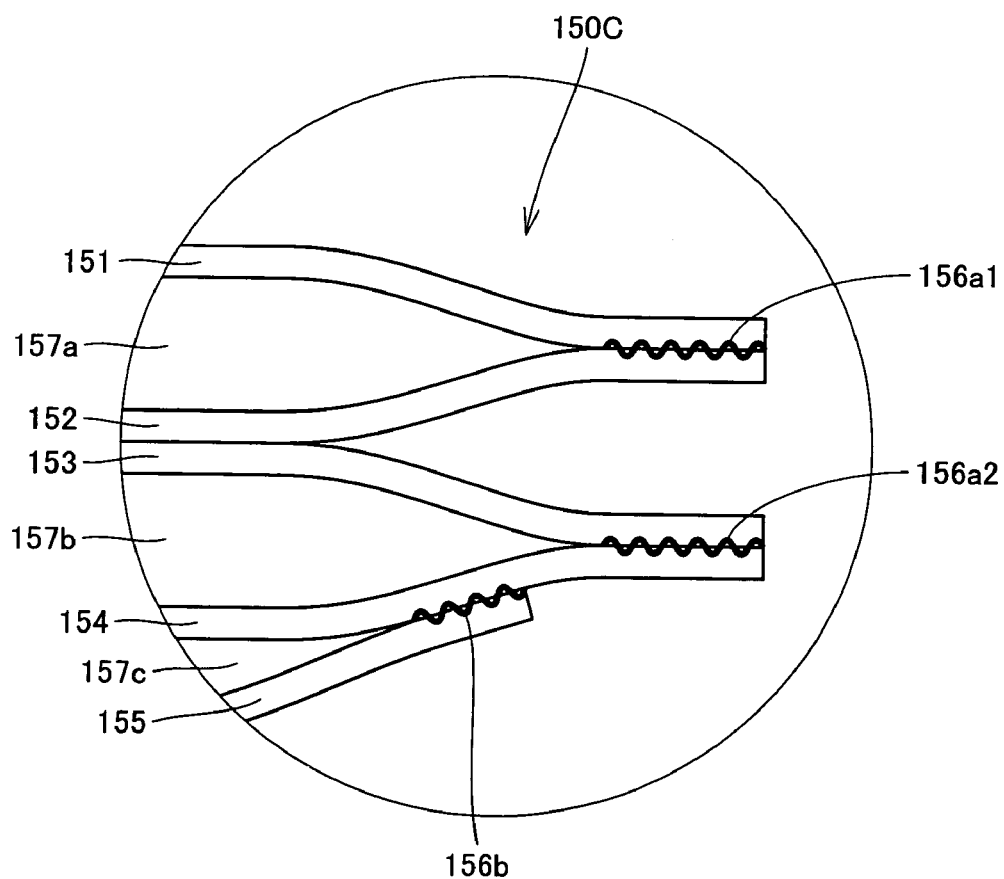
FIG. 11 is an enlarged view of the region XI shown in FIG. 10.

FIG. 10 is a schematic cross sectional view of a cuff for a blood pressure monitor according to Example 3 based on the present embodiment. FIG. 11 is an enlarged view of a region ) shown in FIG. 10. In the following, the portions different from those of Example 1 above will be explained, while description of the similar portions will not be repeated.

As shown in FIG. 10, an air bag 150C contained in a cuff 130C for a blood pressure monitor of the present example is characterized in that the first bag member of air bag 150A contained in 130A for a blood pressure monitor of Example 1 is formed using four resin sheets to have two layers of inflated/deflated spaces.

Air bag 150C includes a first bag member located on the outer side in the thickness direction of air bag 150C in the state where cuff 130C for a blood pressure monitor is mounted on the wrist, and a second bag member positioned on the inner side in the thickness direction of air bag 150C when cuff 130C is mounted on the wrist. The first bag member is formed of four resin sheets 151, 152, 153 and 154, and has first inflated/deflated spaces 157a and 157b therein. First inflated/deflated spaces partitioned by resin sheets 152 and 153 are in communication with each other via a communication hole 159a formed at a prescribed position of resin sheets 152 and 153. The second bag member is formed of two resin sheets 154 and 155, and has a second inflated/deflated space 157c therein. First inflated/deflated space 157b located on the living body side is in communication with second inflated/deflated space 157c via a communication hole 159b provided at a prescribed position of resin sheet 154.

Resin sheet 155 constitutes an inner wall portion of air bag 150C, and resin sheet 151 constitutes an outer wall portion of air bag 150C. A surface on the wrist side of the inner wall portion of air bag 150C functions as a working face 158 for pressing the wrist.

Air bag 150C having the above-described configuration is fabricated, e.g., in the following manner. Two resin sheets 151 and 152 of an approximately rectangular shape in two dimensions are laid one on the other and their rims are melted and bonded to form a bag member, and two resin sheets 153 and 154 of an approximately rectangular shape in two dimensions are laid one on the other and their rims are melted and bonded to form another bag member. The bag members are then laid one on the other and melted and bonded to form the first bag member. Resin sheet 155 of an approximately rectangular shape in two dimensions but narrower in width is laid on the first bag member, and the rim of resin sheet 155 is melted and bonded to a prescribed position of the outer surface of resin sheet 154 of the first bag member. Air bag 150C is thus fabricated.

In air bag 150C contained in cuff 130C for a blood pressure monitor according to the present example, as shown in FIG. 11, a bonded portion 156b that is a joined portion of two resin sheets 154 and 155 forming the second bag member having second inflated/deflated space 157c therein is provided inner than each end in the width direction of first inflated/deflated spaces 157a and 157b formed inside the first bag member. More specifically, bonded portion 156b of resin sheets 154 and 155 is provided closer to the central portion than each end of a region W (see FIG. 10) where first inflated/deflated spaces 157a, 157b are located. This enables resin sheet 155 forming a part of the second bag member to expand with this bonded portion 156b as a base point, and accordingly, the effect equal to the effect explained in Example 1 above can be obtained.

In Examples 1-3 based on the above embodiment, explanation was made to join the resin sheets by melting and bonding. Joining however is not necessarily restricted to melting and bonding; they may of course be adhered using an adhesive. Further, in Examples 1-3 above, the case of laying a plurality of resin sheets one on another and melting and bonding them to form the first bag member has been explained by way of example. The first bag member however does not necessarily have to be formed using a plurality of resin sheets. The air bag may be formed using a single sheet in a cylindrical shape, and the present invention is applicable to such a case as well.

In the embodiment described above, the case of using the double-faced tape to attach the air bag to the curled elastic member has been explained by way of example. However, they do not necessarily have to be secured by adhesion or the like. They may be secured using another method, or they may be left completely unfixed to each other.

In the embodiment described above, the case of applying the present invention to the cuff for use in a wrist blood pressure monitor assuming the wrist as a measurement site has been explained by way of example. The present invention is applicable to a cuff of a blood pressure monitor of any type including an upper arm type and a finger type.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A cuff for a blood pressure monitor having a fluid bag increasing in size in a thickness direction when inflated and decreasing in size in said thickness direction when deflated, wherein said fluid bag includes a first bag member located on an outer side in said thickness direction in a state where the cuff for a blood pressure monitor is fitted on a living body and having a first inflated/deflated space therein, and a second bag member located on an inner side in said thickness direction in the state where the cuff for a blood pressure monitor is fitted on a living body and having a second inflated/deflated space therein, said second bag member is formed by joining a rim of a single-layer sheet-shaped member to an inner surface of said first bag member, the single-layer sheet-shaped member being narrower in width than said first bag member, said second inflated/deflated space is defined by said living body side surface of said first bag member and a main surface of said single-layer sheet-shaped member facing said living body side surface, and said first bag member has ends that delimit a width of said first inflated/deflated space and is joined to said single-layer sheet-shaped member at positions more inward than the ends that delimit the width of said first inflated/deflated space.

2. The cuff for a blood pressure monitor according to claim 1, wherein said single-layer sheet-shaped member is more elastic than a member forming said living body-side surface of said first bag member.

3. The cuff for a blood pressure monitor according to claim 1, wherein a material of said single-layer sheet-shaped member constituting a part of said second bag member is soft polyvinyl chloride, copolymer of ethylene-vinyl acetate, polyurethane, or thermoplastic elastomer olefin.

4. The cuff for a blood pressure monitor according to claim 1, wherein said single-layer sheet-shaped member and a member forming said living body-side surface of said first bag member comprise the same material.

5. The cuff for a blood pressure monitor according to claim 4, wherein said single-layer sheet-shaped member has a thickness smaller than a thickness of said member forming said living body-side surface of said first bag member.

6. The cuff for a blood pressure monitor according to claim 1, wherein said first bag member is formed by joining rims of a plurality of sheet-shaped members to each other.

7. The cuff for a blood pressure monitor according to claim 1, wherein said first inflated/deflated space and said second inflated/deflated space are in communication with each other.

8. A blood pressure monitor, comprising:

a cuff for a blood pressure monitor having a fluid bag increasing in size in a thickness direction when inflated and decreasing in size in said thickness direction when deflated;

an inflating/deflating portion for inflating and deflating said fluid bag;

a pressure detecting portion for detecting a pressure within said fluid bag; and a blood pressure value calculating portion for calculating a blood pressure value based on pressure information detected by said pressure detecting portion; wherein said fluid bag has a first bag member located on an outer side in said thickness direction in a state where said cuff for a blood pressure monitor is fitted on a living body and having a first inflated/deflated space therein, and a second bag member located on an inner side in said thickness direction in the state where said cuff for a blood pressure monitor is fitted on a living body and having a second inflated/deflated space therein, said second bag member is formed by joining a rim of a single-layer sheet-shaped member to an inner surface of said first bag member, the single-layer sheet-shaped member being narrower in width than said first bag member, said second inflated/deflated space is defined by said living body side surface of said first bag member and a main surface of said single-layer sheet-shaped member facing said living body side surface, and said first bag member has ends that delimit a width of said first inflated/deflated space and is joined to said single-layer sheet-shaped member at positions more inward than the ends that delimit the width of said first inflated/deflated space.

9. A cuff for a blood pressure monitor having a fluid bag increasing in size in a thickness direction when inflated and decreasing in size in the thickness direction when deflated, wherein the fluid bag includes a first bag member located on an outer side in the thickness direction in a state where the cuff for a blood pressure monitor is fitted on a living body and having a first inflated/deflated space therein, and a second bag member located on an inner side in the thickness direction in the state where the cuff for a blood pressure monitor is fitted on a living body and having a second inflated/deflated space therein, the second bag member is formed by joining a rim of a single-layer sheet-shaped member to an inner surface of the first bag member so that the single-layer sheet-shaped member is positioned to contact a living body and occlude an artery of a living body when the fluid bag is inflated, and the first bag member has ends that delimit a width of the first inflated/deflated space and is joined to the single-layer sheet-shaped member at positions more inward than the ends that delimit its width.

* * * * *